US011439421B2

(12) United States Patent
Recanati et al.

(10) Patent No.: US 11,439,421 B2
(45) Date of Patent: Sep. 13, 2022

(54) ATRAUMATIC TENACULUM FOR FACILITATION OF TRANSCERVICAL PROCEDURES

(71) Applicants: Maurice Andre Recanati, New York, NY (US); Katherine Kramer, Philadelphia, PA (US); Jay Berman, West Bloomfield, MI (US); Mohammad Ali Ozbeki, Novi, MI (US); John M. Pierick, Jr., Gross Pointe Woods, MI (US); Johney Lee, Monroe, GA (US); Ali Ghazala, Troy, MI (US); Uzair Shah, Canton, MI (US); George Contos, Royal Oak, MI (US)

(72) Inventors: Maurice Andre Recanati, New York, NY (US); Katherine Kramer, Philadelphia, PA (US); Jay Berman, West Bloomfield, MI (US); Mohammad Ali Ozbeki, Novi, MI (US); John M. Pierick, Jr., Gross Pointe Woods, MI (US); Johney Lee, Monroe, GA (US); Ali Ghazala, Troy, MI (US); Uzair Shah, Canton, MI (US); George Contos, Royal Oak, MI (US)

( * ) Notice: Subject to any disclaimer, the term of this patent is extended or adjusted under 35 U.S.C. 154(b) by 87 days.

(21) Appl. No.: 16/747,073

(22) Filed: Jan. 20, 2020

(65) Prior Publication Data
US 2020/0229832 A1 Jul. 23, 2020

Related U.S. Application Data

(60) Provisional application No. 62/793,915, filed on Jan. 18, 2019.

(51) Int. Cl.
*A61B 17/28* (2006.01)
*A61B 17/42* (2006.01)

(52) U.S. Cl.
CPC ........ *A61B 17/282* (2013.01); *A61B 17/2833* (2013.01); *A61B 17/2841* (2013.01);
(Continued)

(58) Field of Classification Search
CPC ... A61B 17/42; A61B 17/282; A61B 17/2833; A61B 2017/4216; A61B 2017/4225;
(Continued)

(56) References Cited

U.S. PATENT DOCUMENTS

| 2,294,852 A | * | 9/1942 | Smith | A61B 17/326 606/118 |
| 2002/0116025 A1 | * | 8/2002 | Haab | A61B 17/02 606/206 |

(Continued)

*Primary Examiner* — Kathleen S Holwerda
*Assistant Examiner* — Lauren Dubose
(74) *Attorney, Agent, or Firm* — Jacob M. Ward; Ward Law Office LLC (57) ABSTRACT

A medical device used for grasping a body tissue has a main body having a first arm rotatably connected to a second arm at a pivot point. The main body has a proximal end and a distal end. A handle portion and a locking portion are disposed at the proximal end of the main body. A gripping portion including at least one flexible member is disposed at a distal end of the main body. The at least one flexible member is one of a flexible silicone band and a first gel-filled silicone pad and a second gel-filled silicone pad.

15 Claims, 7 Drawing Sheets

(52) U.S. Cl.
CPC ...... *A61B 17/42* (2013.01); *A61B 2017/2837* (2013.01); *A61B 2017/4225* (2013.01)

(58) Field of Classification Search
CPC .... A61B 2017/2916; A61B 2017/2917; A61B 2017/2926; A61B 17/2841; A61B 17/326; A61B 17/29; A61B 17/2909; A61B 17/122; A61B 2017/2905; A61B 2017/2945

See application file for complete search history.

(56) References Cited

U.S. PATENT DOCUMENTS

| | | | |
|---|---|---|---|
| 2005/0277959 A1* | 12/2005 | Cosgrove | A61B 17/1285 606/151 |
| 2007/0142844 A1* | 6/2007 | Kotmel | A61B 17/42 606/119 |
| 2008/0039864 A1 | 2/2008 | Feuer et al. | |
| 2009/0012350 A1* | 1/2009 | Tihon | A61F 2/004 600/30 |
| 2012/0010654 A1* | 1/2012 | Staggs | A61B 17/2812 606/213 |
| 2012/0283595 A1 | 11/2012 | Curtis et al. | |
| 2016/0331408 A1 | 11/2016 | Benson et al. | |
| 2017/0172595 A1* | 6/2017 | Lathrop | A61B 34/71 |

\* cited by examiner

ATRAUMATIC TENACULUM FOR FACILITATION OF TRANSCERVICAL PROCEDURES

CROSS-REFERENCE TO RELATED APPLICATIONS

This application claims the benefit of U.S. Provisional Application Ser. No. 62/793,915, filed on Jan. 18, 2019. The entire disclosure of the above application is hereby incorporated herein by reference.

FIELD

The present disclosure relates generally to a medical device used to stabilize a body tissue and, more specifically, to a tenaculum used to stabilize a cervix during a medical procedure.

BACKGROUND

A tenaculum is a medical device that functions to aid a surgeon in gaining transcervical access to the uterine cavity. Gynecologic procedures such as IUD insertion, endometrial biopsy, dilation and curettage, and hysteroscopy require stabilization of the cervix in order to be performed. A tenaculum functions to stabilize and provide countertraction on the cervix while devices are pushed through the cervical os. Traction on the tenaculum reduces the cervico-uterine angle allowing access to the uterus across the cervical os.

The most utilized tenaculum is the single tooth tenaculum. The single tooth tenaculum attaches to cervical tissue through bilateral puncture of the stroma of the cervix. A locking mechanism prevents the device from reopening. While this device securely attaches to the cervix, traction on the device can cause the teeth to rip through tissue and further traumatize the cervix. The cervix receives blood supply from the uterine arteries and is highly vascularized. As a result, trauma to the cervix caused by a single tooth tenaculum can cause complications such as bleeding and infection, longer procedure times, and significant pain and discomfort to patients.

Known tenaculums have been established to address the issues posed by the single tooth tenaculum. For example, U.S. Patent Application No. 2016/0331408 to Benson et al. discloses a tenaculum with footpads containing ridges in order to grasp cervical tissue with traction. In U.S. Patent Application No. 2008/0039864 to Feuer et al., a tenaculum with a cervical os applicator that is inserted into the os with anchors to the outer surface is disclosed. U.S. Patent Application No. 2012/0283595 to Curtis et al. describes a tenaculum that engages the vaginal portion of the cervix, encircles the external os, and distributes uniform negative pressure around the engaged surface of the cervix. Each of these methods have attempted to allow for manipulation of the cervix without traumatic engagement.

There is a continuing need for a medical device that can stabilize the cervix and provide countertraction while performing transcervical procedures without causing bleeding or damage to the cervical tissue or interfering with visualization.

SUMMARY

In concordance with the instant disclosure, a medical device that can stabilize the cervix and provide countertraction while performing transcervical procedures without causing bleeding or damage to the cervical tissue or interfering with visualization, has surprisingly been discovered.

More particularly, the present disclosure relates to a medical device that aids in stabilizing the cervix thereby allowing transcervical access to the uterus, without puncturing tissue, creating cervical trauma, pain or bleeding and without interfering with visualization of the operative field.

In one embodiment, a medical device includes a main body with a first arm rotatably connected to a second arm at a pivot point. The main body has a proximal end and a distal end. A handle portion and a locking mechanism are disposed at the proximal end of the main body. A gripping portion including at least one flexible member is disposed at the distal end of the main body.

In another embodiment, a medical device includes a main body with a first arm rotatably connected to a second arm at a pivot point. The main body has a proximal end and a distal end. A handle portion is disposed at the proximal end of the main body. A locking portion is disposed at the proximal end of the main body and includes one of a ratchet mechanism and a slit and screw mechanism. The locking portion is configured to lock the first arm and the second arm in place in operation. A gripping portion includes a first connecting means disposed at a distal end of the first arm, a second connecting means disposed at a distal end of the second arm, and at least one flexible member.

In a further embodiment, a method of stabilizing a body tissue for a procedure includes selecting a medical device including a main body with a first arm rotatably connected to a second arm at a pivot point. The main body has a proximal end and a distal end. A handle portion and a locking mechanism are disposed at the proximal end of the main body. A gripping portion including at least one flexible member is disposed at the distal end of the main body. The method further includes steps of gripping the handle portion of the medical device, manipulating the handle portion at the proximal end of the medical device to create an opening at the distal end, positioning the at least one flexible member adjacent a body tissue, manipulating the handle portion of the medical device to secure the at least one flexible member to the body tissue, and engaging the locking mechanism of the medical device, performing a medical procedure, disengaging the locking mechanism, manipulating the handle portion at the proximal end of the medical device to create an opening at the distal end, releasing the body tissue from the at least one flexible member, and removing the medical device from the patient.

In yet another embodiment, a medical device includes a handle with substantially circular fingertip holes located at the end of a symmetric main member having a generally rectangular cross section. A ratchet mechanism at a handle end of the device prevents the device from opening and closing. A pin joint made out of a screw or a rivet allows the main members to rotate freely. At an opposite end of the main member, a vertical member offsets each main member to a C-shaped cervical grasper. A gel-filled C-shaped silicone pillow is glued to each grasper and transmits pressure exerted by each grasper onto a larger area on an exterior surface of the cervix.

In yet a further embodiment, a medical device includes main members that have a slit at an end opposite a handle. This slit allows for a stretchable silicone silastic band to fit between the main members. The band encircles a cervix and provides cervical stabilization in an atraumatic fashion. A slit and screw prevent the device from opening once the screw is tightened. The main members are comprised of a substantially straight portion followed by a curvilinear, bowed shape, portion with the pivot point located between these portions.

In yet one more embodiment, the medical devise has a substantially scissor-like shaped body and a handle of sufficient size to permit a comfortable grip that is an integral part of the main member of the device. The handle has a circularly shaped finger grip. The medical device further includes a scissor-like shaped main body and a locking mechanism that is integral to the handle of the device and has mechanism preventing the device from opening or closing once set. The locking mechanism includes a mechanism allowing for rapid release. The locking mechanism may be a slit and screw mechanism which may be tightened as a friction lock or a ratcheting mechanism. A pair of symmetric main members have a substantially rectangular cross section. The medical device is 25-40 cm long and terminates at one end with the handle and locking mechanism and, on the other end, with the cervical grasping mechanism. The symmetric main members are attached using a screw or a rivet and have a substantially straight portion and a curvilinear (bowed) portion with the pivot point separating the two portions. The main members are capable of rotating freely around each other about the screw or rivet. A cervical grasping mechanism has a vertical member allowing the placement of the cervical grasper on a plane higher than the plane of the main members. A substantially C-shaped cervical grasper with a radius of curvature appropriate for human cervix size includes a soft, compressible silicone pillow permanently bonded to the C-shaped cervical grasper. A textured surface on the surface of the compressible silicone pillow maximizes contact area with the cervix.

In yet an additional embodiment, the cervical grasping mechanism includes a slit located at the end of each of the two symmetric main bodies of sufficient length to allow an elastic silicone silastic band to be permanently bonded. The band is of sufficient length to circumscribe the cervix and sufficient width to grip the cervix without slipping. The band is sufficiently soft to prevent cervical tissue trauma and includes a textured surface to maximize contact area with cervical tissue.

In yet a further embodiment, the medical device has no separable parts, the device is safe to use and has no sharp angles, disposable, sterilizable, and inexpensive to manufacture. The device is made of biosafe materials suitable for placement within the human body and can atraumatically attach to the cervix without causing bleeding. The device is capable of securely attaching to the cervix alone or through a vaginal speculum and is easy to apply to the cervix. The device can easily be removed when no longer needed without injuring the cervix and does not interfere with trans-cervical procedures. The device is substantially flat, does not interfere with visualizing the cervix or substantially compress the endocervical canal, facilitates transcervical access to the uterine cavity, and provides traction on the cervix without damaging tissue. The device is capable of fitting through a speculum and can stabilize the cervix without closing the cervical os. The device facilitates insertion of an intrauterine device, an endometrial biopsy device, a hysteroscope, or a suction or sharp curette. The device limits intra and post procedural complications due to bleeding at tenaculum site and can be removed and reapplied easily with reduced risk of tissue injury. The device provides optimal exposure of the endocervical canal and is capable of adjusting to cervixes of any size from 2 cm to 5 cm. The device allows the cervix to be cupped and manipulated.

It should be understood that the medical device is particularly well suited for facilitating IUD insertion, endometrial biopsy, dilation and curettage, and hysteroscopy. This medical device is comprised of two long symmetric members which can rotate about a pivot point. Each member is terminated on one end by a finger grip and ratchet, and on the other end by a means of grasping the uterine cervix. In a first embodiment this comprises a blunt end with a silastic tape. A second embodiment comprises soft, compressible graspers offset on the vertical plane from the symmetric members. Both embodiments can grasp the cervix without the trauma, pain and bleeding associated with existing single tooth tenaculums.

DRAWINGS

The above, as well as other advantages of the present disclosure, will become readily apparent to those skilled in the art from the following detailed description, particularly when considered in the light of the drawings described hereafter.

DETAILED DESCRIPTION

The following detailed description and appended drawings describe and illustrate various embodiments of the invention. The description and drawings serve to enable one skilled in the art to make and use the invention and are not intended to limit the scope of the invention in any manner.

A medical device 2 used to stabilize a cervix 4 (shown in FIGS. 6-9) according to various embodiments of the present disclosure is shown in FIGS. 1-9. The medical device 2 includes a main body 6, a handle portion 8, a locking mechanism 10, and a gripping mechanism 12. The medical device 2 is made from any biosafe material or combination of biosafe materials suitable for placement in a human body such as stainless steel, biosafe plastic, and biosafe silicone, as non-limiting examples. Other suitable materials may also be selected by one skilled in the art within the scope of the present disclosure.

The main body 6 has a proximal end 14 and a distal end 16. In certain embodiments, the main body 6 has a substantially scissor-like shape including a first arm 18 having a proximal end 20 and a distal end 22 and a second arm 24 having a proximal end 26 and a distal end 28. The first arm 18 and the second arm 24 are substantially symmetrical with the proximal ends 20, 26 being substantially straight and the distal ends 22, 28 having a curvilinear or bow shape. In preferred embodiments, the main body 6 measures between twenty-five centimeters (25 cm) and forty centimeters (40 cm). One of ordinary skill in the art may select any other suitable size and shape, including dimensions, for the main body 6 including the first arm 18 and the second arm 24, as desired.

The first arm 18 intersects with the second arm 24 at a crossing section 29. The first arm 18 is rotatably connected to the second arm 24 at a pivot point 30 of the crossing section 29 using any suitable attachment mechanism 32 such as a screw, rivet, or hinge, as non-limiting examples. The pivot point 30 is located centrally in the crossing section 29. The first arm 18 and the second arm 24 rotate freely about the pivot point 30.

Figure 1:
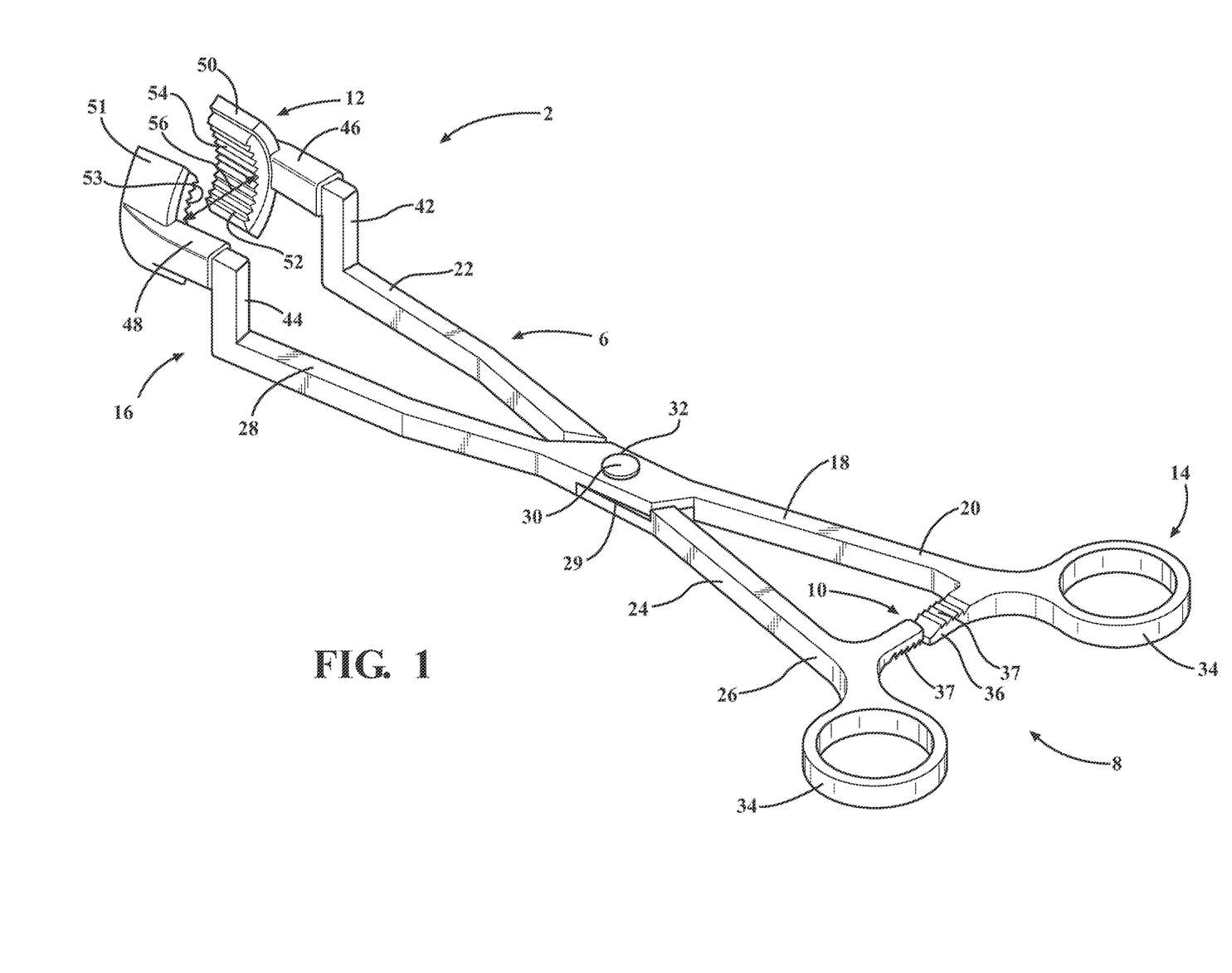
FIG. 1 is a rear perspective view of a tenaculum according to one embodiment of the present disclosure, the tenaculum shown in an open, unlocked position.
Figure 2:
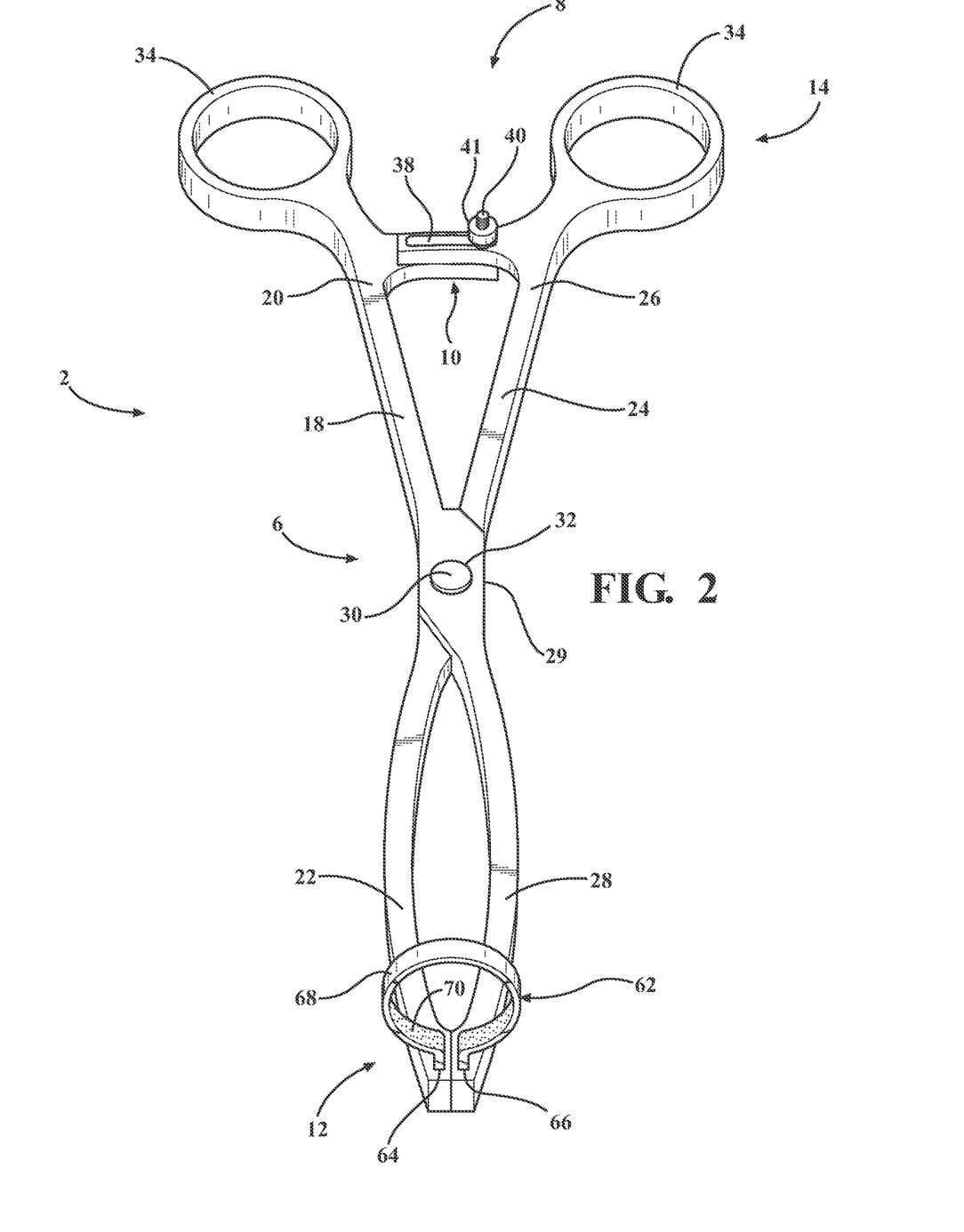
FIG. 2 is a front perspective view of a tenaculum according to another embodiment of the present disclosure, the tenaculum shown in a closed, locked position.
Figure 3:
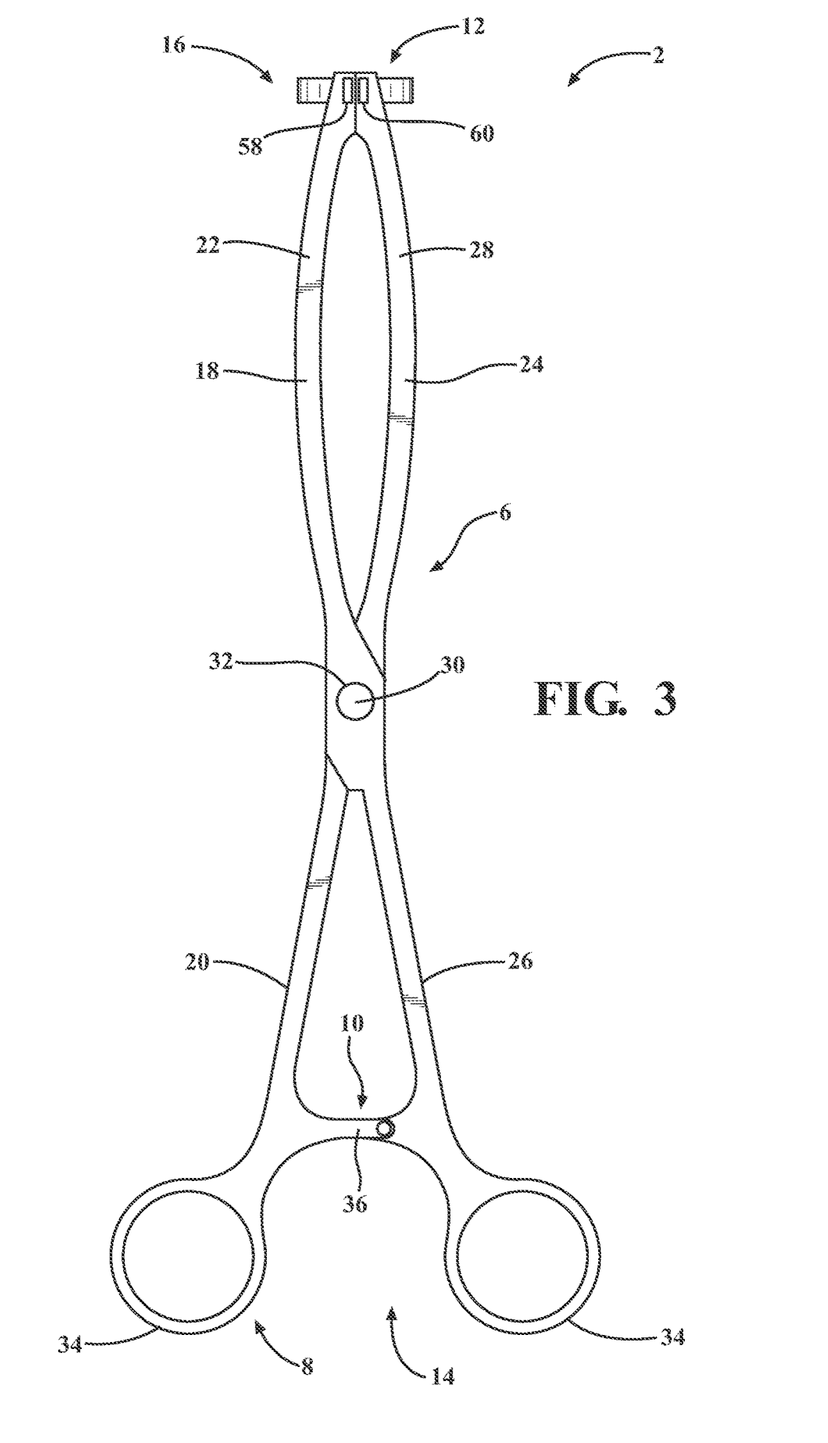
FIG. 3 is a bottom elevational view of the tenaculum shown in FIG. 2.

The handle portion 8 is integral with and disposed adjacent to the proximal end 14 of the main body 6, as shown in FIGS. 1-3, and is configured to provide a comfortable, easy-to-use grip for a user. The user manipulates the handle portion 8 to open and close the gripping mechanism 12, and in some cases to activate and release the locking mechanism 10, in operation.

In certain embodiments, the handle portion includes two finger grips 34, with one disposed adjacent the proximal end 30 of the first arm 18 and the other disposed adjacent the proximal end 26 of the second arm 24. Each finger grip 34 is generally circular or ring-like in shape, in certain embodiments. It should be appreciated that the handle portion 8 is not limited to any particular shape, size, or configuration, and one of ordinary skill in the art may select other suitable configurations having various shapes and sizes for the handle portion 8, as desired.

With renewed reference to FIGS. 1-3, the locking mechanism 10 is disposed at the proximal end 14 of the main body 6. In certain embodiments, the locking mechanism 10 includes a ratchet mechanism 36, as shown in FIG. 1. The ratchet mechanism 36 includes a plurality of teeth 37 disposed on the proximal end 20 of the first arm 18 and the proximal end 26 of the second arm 24. The teeth 37 disposed on the first arm 18 are configured to lockingly engage with the teeth 37 disposed on the second arm 24 such that the user may lock the medical device 2 in a variety of desired positions using the handle portion 8.

Figure 5:
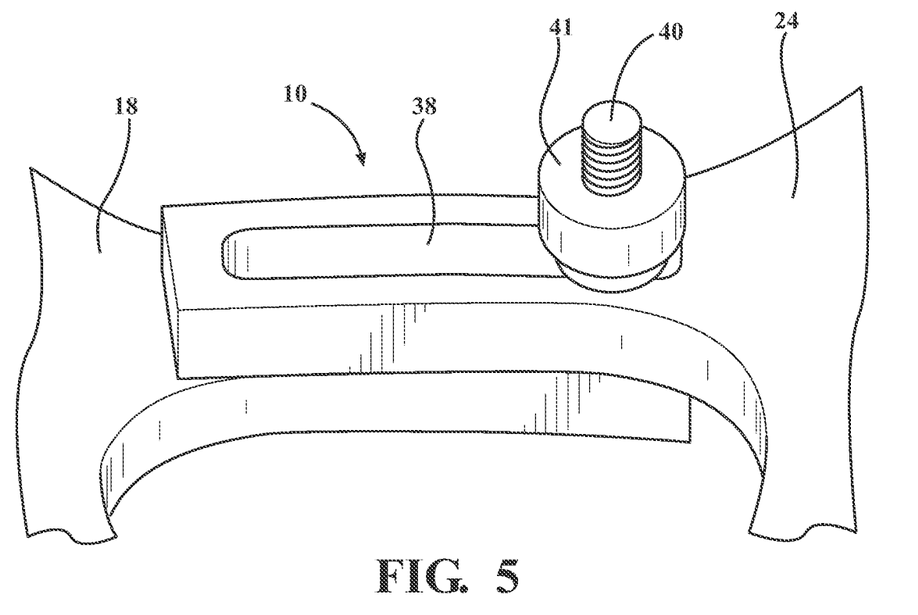
FIG. 5 is an enlarged fragmentary front perspective view of the locking mechanism of the tenaculum shown in FIG. 2, the locking mechanism in a locked position.

In an alternative embodiment, as shown in FIGS. 2, 3, and 5, the locking mechanism 10 includes a channel or slit 38 disposed in the proximal ends 20, 26 of one of the first arm 18 and the second arm 24. As shown in FIG. 5, a screw 40 fastened to a nut 41 may be slidingly disposed in the slit 38, thereby selectively forming a friction lock upon a tightening of the nut 41 on the screw. The nut 41 may include a wing nut (not shown), for example, or any other suitable shape that permits for ease in manual tightening or untightening of the nut 41 by the user in operation. In such case the screw 40 may be permanently affixed to an opposite one of the first arm 18 and the second arm 24 and laterally slidably disposed within the slit 38 where the nut 41 is not sufficiently tightened. This arrangement advantageously permits for a selective locking of the device 2 in a particular position in operation.

In an alternative embodiment, the screw 40 and the slit 38 form a friction lock when the screw 40 is wedged into a narrowed portion of the slit 38 (not shown). It should be appreciated that any other suitable locking mechanism 10 configured to lock the first arm 18 and the second arm 24 in place, thereby preventing rotation about the pivot point 30, may also be employed within the scope of the present disclosure. It should be understood that the locking mechanism 10 in preferred embodiments includes a mechanism (not shown) for rapid release.

As shown in FIG. 1, the gripping mechanism 12 may be integral with and disposed adjacent the distal end 16 of the main body 6. In a particular embodiment, the gripping mechanism 12 includes a first projection 42 extending vertically upward from the distal end 22 of the first arm 18 and a second projection 44 extending vertically upward from the distal end 28 of the second arm 24. In certain embodiments, each of the first and second projections 42, 44 extends vertically upward from the distal ends 22, 28 at an approximately 90-degree angle, respectively. One of ordinary skill in the art may determine that the first and second projections 42, 44 should extend vertically upward from the distal ends 22, 28 at other various angles, as desired, and in certain embodiments each of the first and second projections 42, 44 may further be adjustable with respect to the distal ends 22, 28.

A first connector 46 extends outwardly from the first projection 42 and a second connector 48 extends outwardly from the second projection 44. In certain embodiments, the first and second connectors 46, 48 extend outwardly on a plane that is parallel to a plane on which the first and second arms 18, 24 are located. It should be understood that placement of the first and second projections 42, 44 relative to the first and second arms 18, 24 and placement of the first and second connectors 46, 48 relative to the first and second projections 42, 44 and the first and second arms 18, 24 may vary according to different embodiments and as determined by one of ordinary skill in the art. In certain embodiments, each of the first and second connectors 46, 48 may be adjustable with respect to the first and second projections 42, 44.

Figures 8, 9:
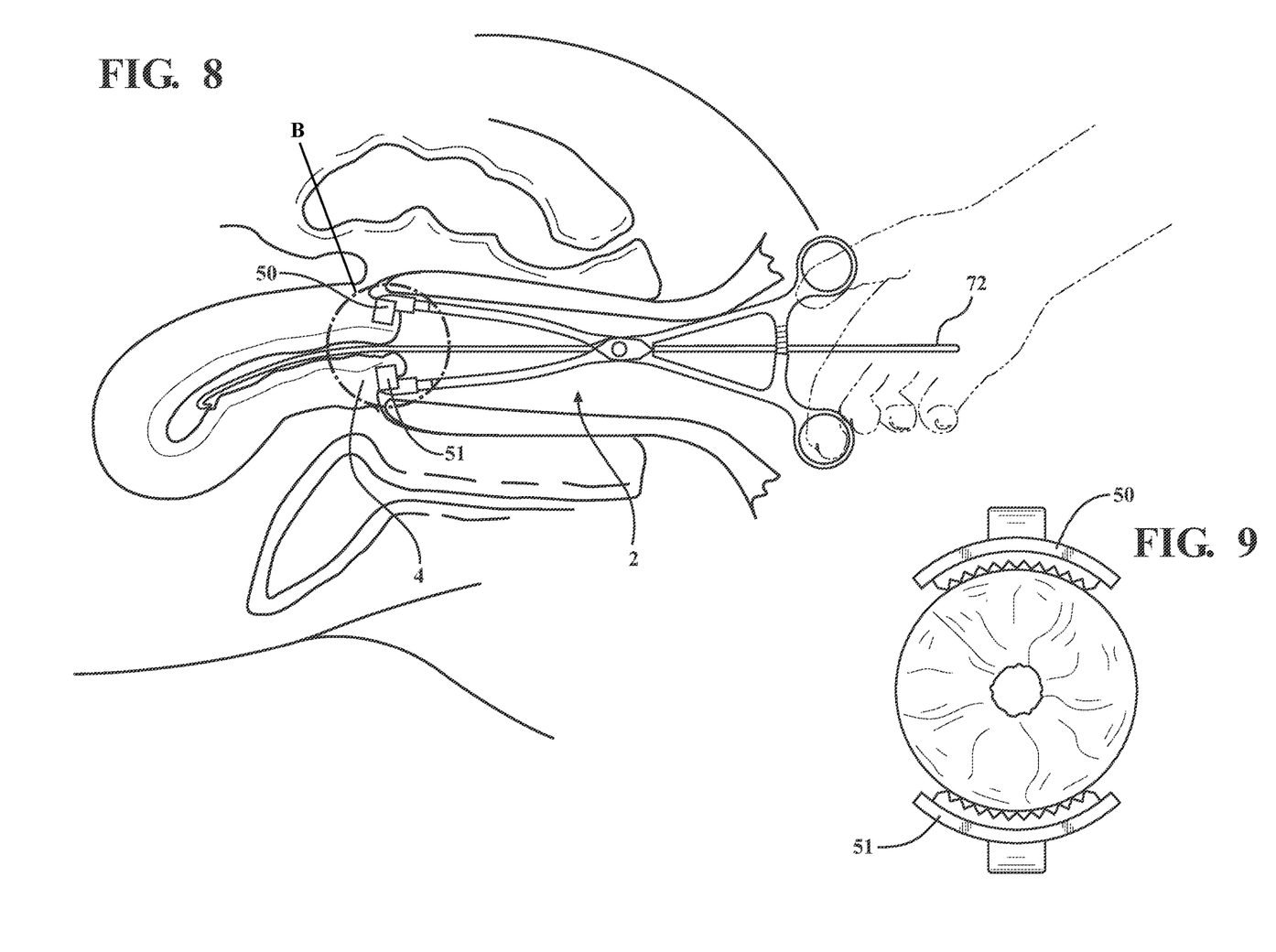
FIG. 8 is a side elevational view of the tenaculum of FIG. 1 in use in a patient, the tenaculum grasping and stabilizing the patient's cervix.
FIG. 9 is an enlarged front elevational view of the tenaculum taken at callout B in FIG. 8, the tenaculum grasping and stabilizing the patient's cervix.

As shown in FIGS. 1 and 8-9, a first C-shaped member 50 is integral with and extends outwardly from the first connector 46. Likewise, a second C-shaped member 51 is integral with and extends outwardly from the second connector 48. In certain embodiments, the first and second C-shaped members 50, 51 may be adjustable with respect to the first and second connectors 46, 48, respectively.

In preferred embodiments, a first flexible member 52 is permanently bonded to the first C-shaped member 50 and a second flexible member 53 is permanently bonded to the second C-shaped member 51. The first and second flexible members 52, 53 may be permanently bonded to the first and second C-shaped members 50, 51 using biosafe adhesive as a non-limiting example. One of ordinary skill in the art may select suitable biosafe adhesives as desired.

A textured inner surface 54 of the first flexible member 52 and a textured inner surface of the second flexible member 53 are adapted to maximize the atraumatic contact with the cervix 4.

In a most particular embodiment, the first and second flexible members 52, 53 are soft, compressible, biosafe gel-filled silicone pads or pillows. It should be understood that any biosafe, soft, compressible material capable of transmitting a pressure exerted by the gripping mechanism 12 onto a maximized area of the cervix 4 without pinching or puncturing the cervix 4 may be used for the first and second flexible members 52, 53.

The first and second C-shaped members 50, 51 may each have a radius of curvature that is suitable for the typical cervix 4. More specifically, the first and second C-shaped members 50, 51 have a radius of curvature that is suitable for the cervix 4 measuring between one centimeter (1 cm) and ten centimeters (10 cm), and, most specifically, for the cervix 4 measuring between two centimeters (2 cm) and five centimeters (5 cm). Likewise, an opening 56 between the first and second flexible members 52, 53 has a length that is suitable for the typical cervix 4.

Figure 4:
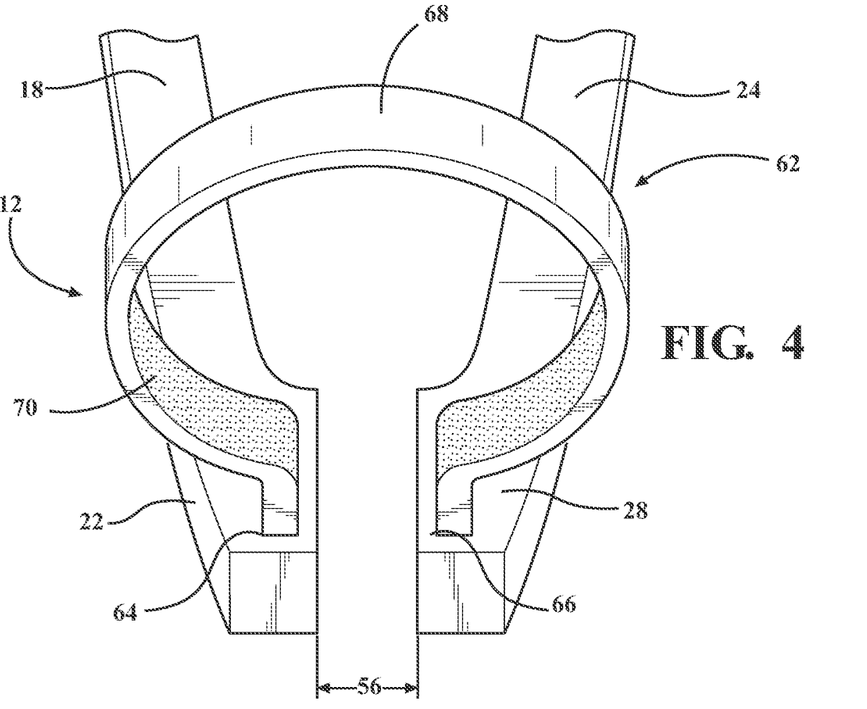
FIG. 4 is an enlarged fragmentary front perspective view of the gripping mechanism of the tenaculum shown in FIG. 2, the gripping mechanism in a partially open position.

As shown in FIGS. 2 and 4, a flexible member 62 may include a substantially ring-shaped band 68. It should be appreciated that the substantially ring-shaped band 68 is not entirely closed, so as to permit its opening and closing by the device 2 for interaction with the cervix 4. The ring-shaped band 68 may be disposed between the first and second ends 64, 66 that is configured to wrap around the cervix 4 in use. The flexible member 62 has a first end 64 that is one of integral with or permanently bonded to the first connector 58, and a second end 66 that is one of integral with or permanently bonded to the second connector 60.

In a particular embodiment, as shown in FIGS. 2-7, the substantially ring-shaped band 68 may be separately formed and then permanently bonded to the first and second ends 64, 66. For example, the distal end 22 of the first arm 18 may have a first connector 58 and the distal end 28 of the second arm 24 may have a second connector 60 disposed therein. In certain embodiments, the first and second connectors 58, 60 are slits formed in the distal ends 22, 28 of the first and second arms 18, 24, respectively, in which the first and second ends 64, 66 of the flexible member 62 are disposed. The first and second ends 64, 66 of the flexible member 62 may be permanently bonded within the slits, for example.

The flexible member 62 including the gel-filled silicone pads or pillows (shown in FIG. 1) or the substantially ring-shaped band (shown in FIG. 2) may further have a textured inner surface 70. The textured inner surface 70 of the flexible member 62 is adapted to maximize contact with the cervix 4. For example, the textured inner surface 70 may be a rubberized surface formed from a medical grade polymer such as silicone. The textured inner surface 70 may include grooves formed into the pillows or the band 68, or in other examples may include nodules or bumps formed into the pillows or the band 68.

It should be appreciated that the flexible member 62 has a suitable length adapted to circumscribe the cervix 4 and a suitable width adapted to grip the cervix 4 without slipping. In a most particular embodiment, the flexible member 62 is made from biosafe silicone or any other soft, biosafe material capable of grasping the cervix 4 atraumatically.

Figure 10:
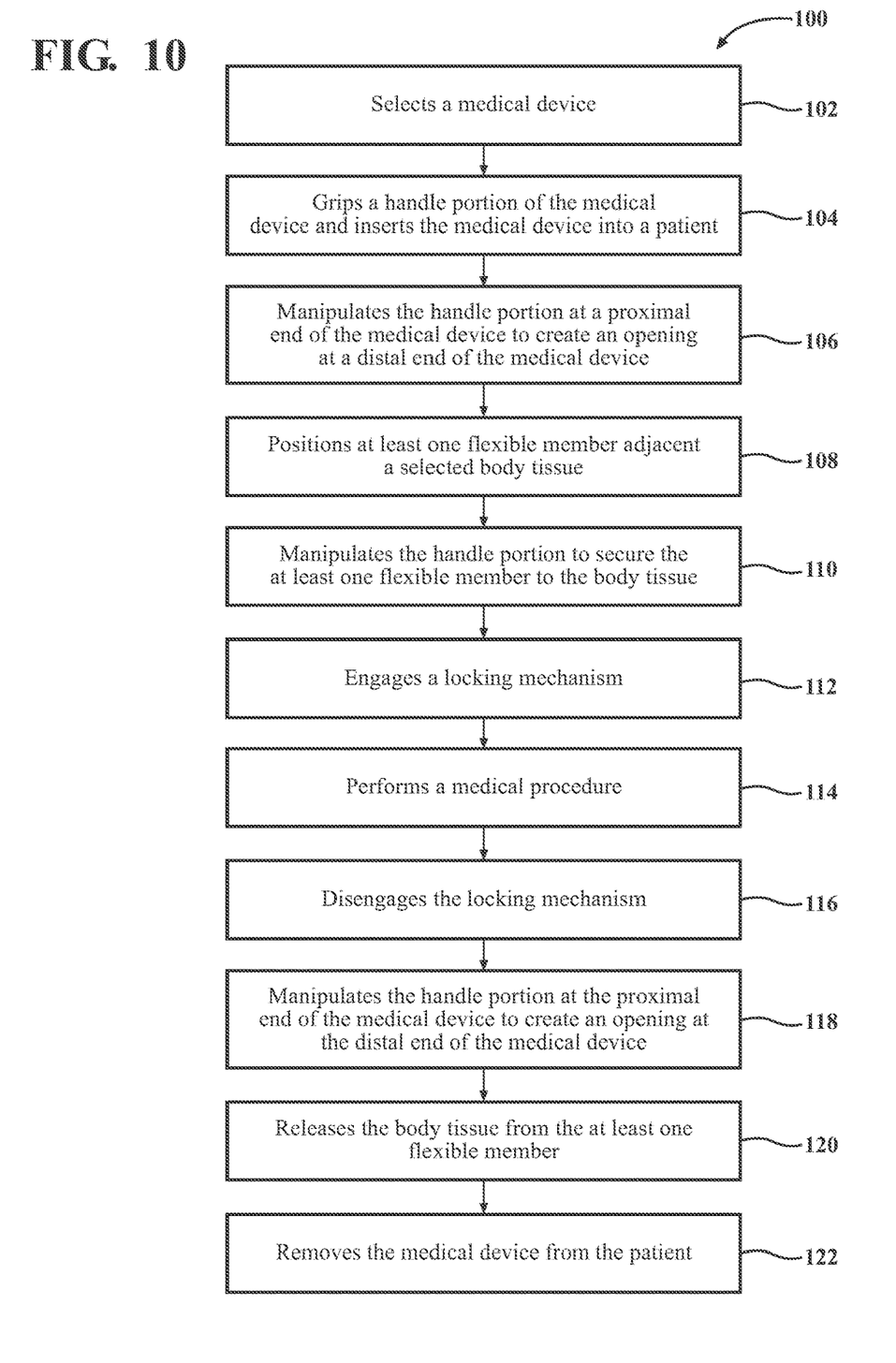
FIG. 10 is a diagram illustrating a method for using the tenaculum of FIGS. 1-9.

With reference to FIG. 10, a method 100 of using the medical device 2 according to various embodiments of the invention is described herein. In first step 102, the user selects the medical device 2. In a second step 104, the user grips the finger grips 34 of the handle portion 8 and inserts the medical device 2 into the patient. The user then manipulates the handle portion 8 at the proximal end 14 of the main body 6 in a third step 106 to move the distal ends 22, 28 of the first and second arms 18, 24 and create the opening 56 having a sufficient width to allow the gripping mechanism 12 to circumscribe the cervix 4. Next, according to one embodiment of the invention, the user positions in a fourth step 108 the flexible members 52, 53 adjacent the cervix 4 and manipulates in a fifth step 110 the handle portion 8 to atraumatically secure the flexible members 52, 53 to the cervix 4. Using an alternative embodiment, the user positions in an alternative fourth step 108 the flexible member 62 adjacent the cervix 4 and manipulates in the fifth step 110 the handle portion 8 to atraumatically circumscribe and secure the flexible member 62 to the cervix 4. Next, the user engages the locking mechanism in a sixth step 112 and performs a medical procedure in a seventh step 114. Upon completion, the user disengages the locking mechanism in an eight step 116 and manipulates the handle portion 8 at the proximal end 14 of the medical device 2 in a ninth step 118 to release the cervix 4 from the gripping mechanism 12 in a tenth step 120. Finally, the user removes the medical device 2 from the patient in an eleventh step 122 of the method 100.

Figures 6, 7:
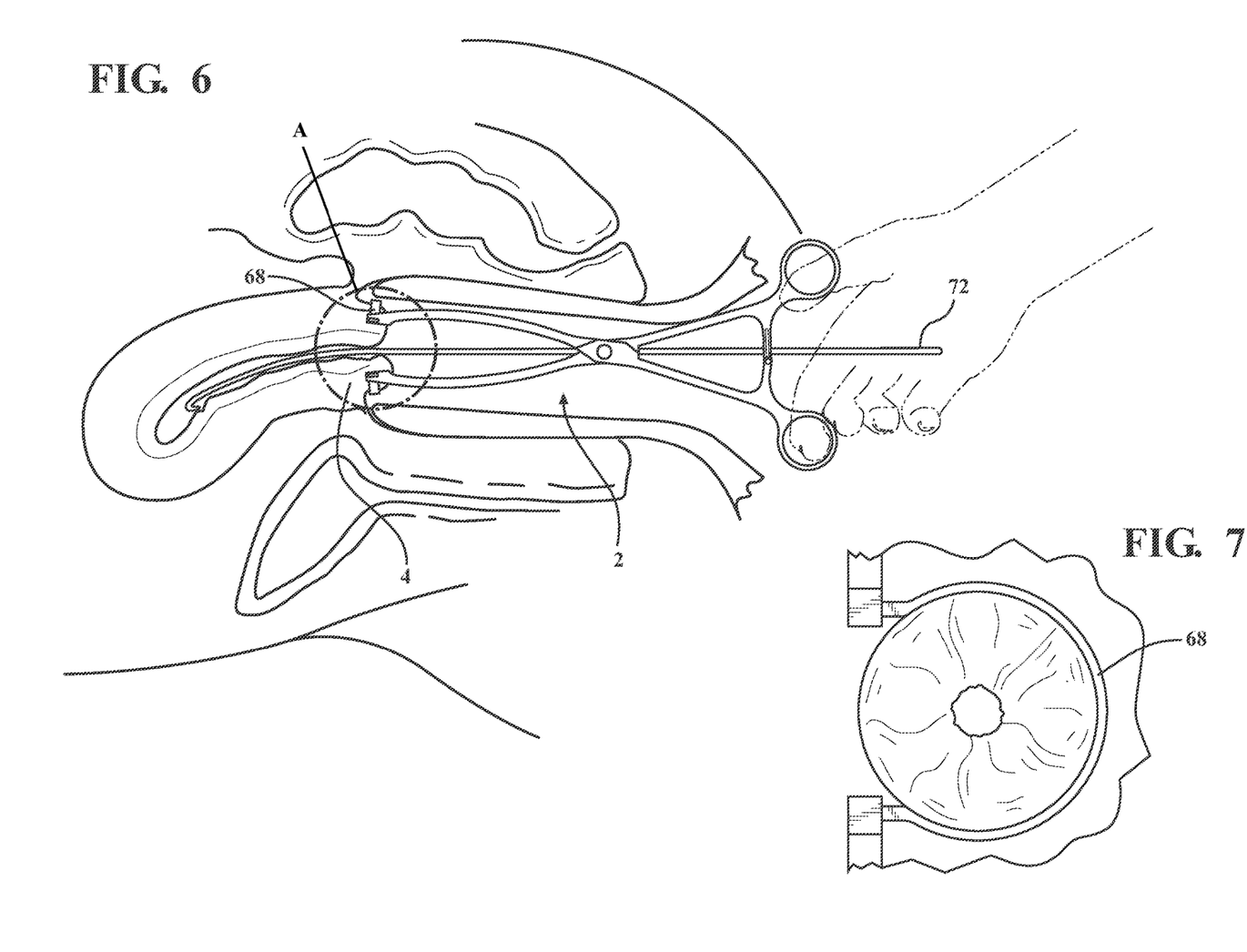
FIG. 6 is a side elevational view of the tenaculum of FIG. 2 in use in a patient, the tenaculum grasping and stabilizing the patient's cervix.
FIG. 7 is an enlarged front elevational view of the tenaculum taken at callout A in FIG. 6, the tenaculum grasping and stabilizing the patient's cervix.

It should be appreciated that the medical device 2 facilitates insertion of a surgical device 72, shown in FIGS. 6 and 8, such as an intrauterine device, an endometrial biopsy device, a hysteroscope, or a suction or sharp curette as non-limiting examples. The medical device 2 is capable of fitting through a speculum and can stabilize the cervix 4, for example, as shown in FIGS. 7 and 9, without closing the cervical os.

It should also be appreciated that the medical device 2, in preferred embodiments, has no separable parts and no sharp projections or angles that may cause harm to the cervix 4 or a surrounding area. The medical device 2 may be disposable or reusable and is sterilizable and inexpensive to manufacture.

Advantageously, the medical device 2 easily and atraumatically attaches to the cervix 4 and provides traction without causing damage and bleeding. The medical device 2 can easily be released from the cervix 4 and removed and reapplied by the user without injuring the cervix and without interfering with trans-cervical procedures. The medical device 2 is substantially flat and the flexible members 52, 53, 62 are positioned in such a manner so as not to interfere with visualizing the cervix 4.

While certain representative embodiments and details have been shown for purposes of illustrating the invention, it will be apparent to those skilled in the art that various changes may be made without departing from the scope of the disclosure, which is further described in the following appended claims.

What is claimed is:

1. A medical device, comprising:
    a main body having a first arm rotatably connected to a second arm at a pivot point, the main body and each of the first arm and the second arm having a proximal end and a distal end;
    a handle portion disposed at the proximal end of the main body;
    a locking mechanism disposed at the proximal end of the main body; and
    a gripping portion including a flexible member disposed at the distal end of the main body, the flexible member having a first end and a second end,
    wherein the distal end of the first arm has a top surface, a bottom surface, and a first connector channel, the first connector channel extending through the distal end of the first arm from the top surface of the first arm to the bottom surface of the first arm,
    wherein the distal end of the second arm has a top surface, a bottom surface, and a second connector channel, the second connector channel extending through the distal end of the second arm from the top surface of the second arm to the bottom surface of the second arm, wherein the first end of the flexible member is disposed within the first connector channel, and the second end of the flexible member is disposed within the second connector channel, wherein the flexible member has a ring-shaped portion, and wherein the first end of the flexible member has a first straight portion extending downwardly from the ring-shaped portion and into the first connector channel, and wherein the second end of the flexible member has a second straight portion extending downwardly from the ring-shaped portion and into the second connector channel, and wherein the flexible member is a flexible silicone band, and the first straight portion of the first end of the flexible member is permanently affixed within the first connector channel of the distal end of the first arm, and the second straight portion of the second end of the flexible member is permanently affixed within the second connector channel of the distal end of the second arm.

2. The medical device of claim 1, wherein the medical device is made from a biosafe material, the biosafe material being at least one of stainless steel, medical grade plastic, and medical grade silicone.

3. The medical device of claim 1, wherein the first arm is rotatably connected to the second arm using one of a screw, a rivet, and a hinge.

4. The medical device of claim 1, wherein the locking mechanism includes a ratchet mechanism configured to lock the first arm and the second arm in place in operation.

5. The medical device of claim 1, wherein the flexible silicone band has a textured inner surface configured to maximize contact with and stabilize a body tissue.

6. The medical device of claim 1, wherein the locking mechanism is a friction lock including a slit and a screw configured to lock the first arm and the second arm in place in operation.

7. A medical device, comprising:
a main body having a first arm rotatably connected to a second arm at a pivot point, the main body and each of the first arm and the second arm having a proximal end and a distal end;
a handle portion disposed at the proximal end of the main body;
a locking mechanism disposed at the proximal end of the main body, the locking portion including either a ratchet mechanism or a slit and screw mechanism configured to lock the first arm and the second arm in place in operation; and
a gripping portion including a flexible member disposed at the distal end of the main body, the flexible member having a first end and a second end,
wherein the distal end of the first arm has a top surface, a bottom surface, and a first connector channel, the first connector channel extending through the distal end of the first arm from the top surface of the first arm to the bottom surface of the first arm,
wherein the distal end of the second arm has a top surface, a bottom surface, and a second connector channel, the second connector channel extending through the distal end of the second arm from the top surface of the second arm to the bottom surface of the second arm,
wherein the first end of the flexible member is disposed within the first connector channel, and the second end of the flexible member is disposed within the second connector channel disposed at the distal end of the main body, wherein the flexible member has a ring-shaped portion, and wherein the first end of the flexible member has a first straight portion extending downwardly from the ring-shaped portion and into the first connector channel, and wherein the second end of the flexible member has a second straight portion extending downwardly from the ring-shaped portion and into the second connector, and wherein the first straight portion of the first end of the flexible member is permanently affixed within the first connector channel of the distal end of the first arm, and the second straight portion of the second end of the flexible member is permanently affixed within the second connector channel of the distal end of the second arm.

8. The medical device of claim 7, wherein the flexible member is a flexible silicone band.

9. A method of stabilizing a body tissue of a patient using a medical device, the method comprising steps of:
providing the medical device comprising:
a main body having a first arm rotatably connected to a second arm at a pivot point, the main body and each of the first arm and the second arm having a proximal end and a distal end;
a handle portion disposed at the proximal end of the main body;
a locking mechanism disposed at the proximal end of the main body; and
a gripping portion including a flexible member disposed at the distal end of the main body, the flexible member having a first end and a second end,
wherein the distal end of the first arm has a top surface, a bottom surface, and a first connector channel, the first connector channel extending through the distal end of the first arm from the top surface of the first arm to the bottom surface of the first arm,
wherein the distal end of the second arm has a top surface, a bottom surface, and a second connector channel, the second connector channel extending through the distal end of the second arm from the top surface of the second arm to the bottom surface of the second arm,
wherein the first end of the flexible member is disposed within the first connector channel, and the second end of the flexible member is disposed within the second connector channel,
wherein the flexible member has a ring-shaped portion, and wherein the first end of the flexible member has a first straight portion extending downwardly from the ring-shaped portion and into the first connector channel, and wherein the second end of the flexible member has a second straight portion extending downwardly from the ring-shaped portion and into the second connector channel, and
wherein the flexible member is a flexible silicone band, and the first straight portion of the first end of the flexible member is permanently affixed within the first connector channel of the distal end of the first arm, and the second straight portion of the second end of the flexible member is permanently affixed within the second connector channel of the distal end of the second arm;
gripping the handle portion of the medical device;
manipulating the handle portion at the proximal end of the medical device to create an opening at the distal end;
positioning the flexible member adjacent the body tissue of the patient;

manipulating the handle portion of the medical device to secure the flexible member to the body tissue;
engaging the locking mechanism of the medical device;
performing a medical procedure;
disengaging the locking mechanism;
manipulating the handle portion at the proximal end of the medical device to create the opening at the distal end;
releasing the body tissue from the flexible member; and
removing the medical device from the patient.

10. The method of claim 9, wherein the flexible member is a flexible silicon band.

11. The medical device of claim 1, wherein the first connector channel has a first opening formed in the top surface of the distal end of the first arm and a second opening formed in the bottom surface of the distal end of the first arm, and wherein the second connector channel has a first opening formed in the top surface of the distal end of the second arm and a second opening formed in the bottom surface of the distal end of the second arm.

12. The medical device of claim 11, wherein the first straight portion of the first end of the flexible member has a first terminal end surface that is flush with the bottom surface of the distal end of the first arm adjacent the second opening formed in the bottom surface of the distal end of the first arm, and wherein the second straight portion of the second end of the flexible member has a second terminal end surface that is flush with the bottom surface of the distal end of the second arm adjacent the second opening formed in the bottom surface of the distal end of the second arm.

13. A medical device, comprising:
a main body having a first arm rotatably connected to a second arm at a pivot point, the main body and each of the first arm and the second arm having a proximal end and a distal end;
a handle portion disposed at the proximal end of the main body;
a locking mechanism disposed at the proximal end of the main body; and
a gripping portion including a flexible member disposed at the distal end of the main body, the flexible member having a first end and a second end,
wherein the distal end of the first arm has a top surface, a bottom surface, and a first connector channel, the first connector channel extending through the distal end of the first arm from the top surface of the first arm to the bottom surface of the first arm,
wherein the distal end of the second arm has a top surface, a bottom surface, and a second connector channel, the second connector channel extending through the distal end of the second arm from the top surface of the second arm to the bottom surface of the second arm,
wherein the first end of the flexible member is disposed within the first connector channel, and the second end of the flexible member is disposed within the second connector channel,
wherein the flexible member has a ring-shaped portion, and wherein the first end of the flexible member has a first straight portion extending downwardly from the ring-shaped portion and into the first connector channel, and wherein the second end of the flexible member has a second straight portion extending downwardly from the ring-shaped portion and into the second connector channel,
wherein the first connector channel has a first opening formed in the top surface of the distal end of the first arm and a second opening formed in the bottom surface of the distal end of the first arm, and wherein the second connector channel has a first opening formed in the top surface of the distal end of the second arm and a second opening formed in the bottom surface of the distal end of the second arm,
wherein the first straight portion of the first end of the flexible member has a first terminal end surface that is flush with the bottom surface of the distal end of the first arm adjacent the second opening formed in the bottom surface of the distal end of the first arm, and wherein the second straight portion of the second end of the flexible member has a second terminal end surface that is flush with the bottom surface of the distal end of the second arm adjacent the second opening formed in the bottom surface of the distal end of the second arm, and
wherein the first straight portion of the flexible member has a first length, the second straight portion of the flexible member has a second length, the first connector channel formed in the distal end of the first arm has a first depth, and the second connector channel formed in the distal end of the second arm has a second depth, the first length of the first straight portion of the flexible member being greater than the first depth of the first connector channel, and the second length of the second straight portion of the flexible member being greater than the second depth of the second connector channel, wherein the ring-shaped portion of the flexible member is offset from the distal end of the first arm and the distal end of the second arm.

14. The medical device of claim 13, wherein the first straight portion is oriented orthogonal with the top surface of the distal end of the first arm, and the second straight portion is oriented orthogonal with the top surface of the distal end of the second arm.

15. A medical device, comprising:
a main body having a first arm rotatably connected to a second arm at a pivot point, the main body and each of the first arm and the second arm having a proximal end and a distal end;
a handle portion disposed at the proximal end of the main body;
a locking mechanism disposed at the proximal end of the main body; and
a gripping portion including a flexible member disposed at the distal end of the main body, the flexible member having a first end and a second end,
wherein the distal end of the first arm has a top surface, a bottom surface, and a first connector channel, the first connector channel extending through the distal end of the first arm from the top surface of the first arm to the bottom surface of the first arm,
wherein the distal end of the second arm has a top surface, a bottom surface, and a second connector channel, the second connector channel extending through the distal end of the second arm from the top surface of the second arm to the bottom surface of the second arm, and
wherein the first end of the flexible member is disposed within the first connector channel, and the second end of the flexible member is disposed within the second connector channel,
wherein the flexible member has a ring-shaped portion, and wherein the first end of the flexible member has a first straight portion extending downwardly from the ring-shaped portion and into the first connector channel, and wherein the second end of the flexible member has a second straight portion extending downwardly from the ring-shaped portion and into the second connector channel, and wherein the first straight portion of the flexible member is permanently bonded within the first connector channel of the distal end of the first arm, and the second straight portion of the flexible member is permanently bonded within the second connector channel of the distal end of the second arm.

\* \* \* \* \*